(12) United States Patent
    Sorensen et al.

(10) Patent No.: US 10,233,328 B2
(45) Date of Patent: Mar. 19, 2019

(54) SOL-GEL BASED MATRIX

(71) Applicant: KØBENHAVNS UNIVERSITET, Copenhagen K (DK)

(72) Inventors: Thomas Just Sorensen, Copenhagen S (DK); Martin Rosenberg, Copenhagen K (DK); Bo W. Laursen, Roskilde (DK)

(73) Assignee: Kobenhavns Universitet, Copenhagen K (DK)

( * ) Notice: Subject to any disclaimer, the term of this patent is extended or adjusted under 35 U.S.C. 154(b) by 0 days.

(21) Appl. No.: 15/028,600

(22) PCT Filed: Oct. 24, 2014

(86) PCT No.: PCT/DK2014/050351
§ 371 (c)(1),
(2) Date: Apr. 11, 2016

(87) PCT Pub. No.: WO2015/058778
PCT Pub. Date: Apr. 30, 2015

(65) Prior Publication Data
US 2016/0251516 A1    Sep. 1, 2016

(30) Foreign Application Priority Data
Oct. 24, 2013   (DK) .................................. 2013 70617

(51) Int. Cl.
| | | |
|---|---|---|
| C08G 77/06 | (2006.01) | |
| C08L 83/06 | (2006.01) | |
| G01N 21/80 | (2006.01) | |
| C08L 83/04 | (2006.01) | |
| C09B 67/00 | (2006.01) | |
| G01N 21/78 | (2006.01) | |
| C09B 11/12 | (2006.01) | |
| C09B 57/00 | (2006.01) | |
| C09B 69/00 | (2006.01) | |
| C09B 69/10 | (2006.01) | |
| C08G 77/08 | (2006.01) | |
| C08G 77/14 | (2006.01) | |
| G01N 21/77 | (2006.01) | |
| B01L 3/00 | (2006.01) | |

(52) U.S. Cl.
CPC .............. *C08L 83/06* (2013.01); *C08L 83/04* (2013.01); *C09B 11/12* (2013.01); *C09B 57/00* (2013.01); *C09B 68/28* (2013.01); *C09B 68/4475* (2013.01); *C09B 69/008* (2013.01); *C09B 69/109* (2013.01); *G01N 21/78* (2013.01); *G01N 21/80* (2013.01); *B01L 3/5082* (2013.01); *C08G 77/08* (2013.01); *C08G 77/14* (2013.01); *C08L 2205/02* (2013.01); *G01N 2021/7756* (2013.01); *G01N 2021/7786* (2013.01)

(58) Field of Classification Search
CPC ...... C08L 183/06; C08L 183/04; C08G 77/06
See application file for complete search history.

(56) References Cited

U.S. PATENT DOCUMENTS

| | | | | |
|---|---|---|---|---|
| 6,858,294 | B1 * | 2/2005 | Tanaka .................... | G02B 1/105 |
| | | | | 428/329 |
| 2004/0157078 | A1 * | 8/2004 | Yoshida ............... | B41M 5/5254 |
| | | | | 428/524 |

FOREIGN PATENT DOCUMENTS

| | | | |
|---|---|---|---|
| WO | WO-2009020259 A1 | | 2/2009 |
| WO | 2009/118271 | * | 10/2009 |
| WO | WO-2009118271 A1 | | 10/2009 |

OTHER PUBLICATIONS

Wencel D et al: "High Performance Optical Ratiometric Sol-Gel-Based PH Sensor", Sensors and Actuators B: Chemical: International Journal devoted to research and development of physical and chemical transducers. Elsevier S.A. CH. vol. 139. No. 1. May 20, 2009 (May 20, 2009). pp. 208-213.

Duong et al: "An Optical PH Sensor with Extended Detection Range Based on Fluoresceinamine Covalently Bound to Sol-Gel Support", Microchemical Journal. New York. NY. US. vol. 84. No. 1-2. Sep. 1, 2006 (Sep. 1, 2006). pp. 50-55.

Lobnik et al: "PH Optical Sensors Based on Sol-Gels. Chemical Doping Versus Covalent Immobilization", Analytica Chimica Acta. Elsevier. Amsterdam. NL vol. 367. No. 1-3. Jan. 1, 1998 (Jan. 1, 1998 ). pp. 159-165.

(Continued)

*Primary Examiner* — Margaret G Moore
(74) *Attorney, Agent, or Firm* — Harness, Dickey & Pierce, P.L.C.

(57) ABSTRACT

The present invention relates to a method for the production of a sol-gel based matrix. The method comprises the steps of: a) providing a first alkoxysilane of the general formula: $R^1$—$Si(OR^2)_3$ and a second alkoxysilane of the general formula (I): b) preparing a first sol-gel component by polymerization of the first alkoxysilane in the presence of an acid catalyst, c) preparing a second sol-gel component by polymerization of the second alkoxysilane in the presence of an Lewis acid catalyst, d) Mixing the first sol-gel component and the second sol-gel component for the preparation of a sol-gel based matrix. The above method results in a sol-gel based matrix with high stability and high porosity. The sol-gel based material may be used for the production of a composite or sensor suitable for monitoring analytes. Methods for preparing these composites or sensors are provided as well.

12 Claims, 7 Drawing Sheets

(56) References Cited

OTHER PUBLICATIONS

Mikkelsen et al: "Controlled Deposition of Sol-gel Sensor Material Using Hemiwicking"; Journal of Micromechanics & Microengineering. Institute of Physics Publishing. Bristol. GB. vol. 21. No. 11. Oct. 5, 2011 (Oct. 5, 2011). p. 115008.
International Search Report regarding Application No. PCT/DK2014/050351, dated Feb. 10, 2015.
Written Opinion regarding Application No. PCT/DK2014/050351, dated Feb. 10, 2015.

* cited by examiner

SOL-GEL BASED MATRIX

CROSS-REFERENCE TO RELATED APPLICATIONS

This application is a U.S. National Phase Application under 35 U.S.C. 371 of International Application No. PCT/DK2014/050351, filed Oct. 24, 2014, and published in English as WO 2015/058778 A1 on Apr. 30, 2015. This application is based on and claims priority to Danish Patent Application No. PA 2013 70617, filed Oct. 24, 2013. The entire disclosures of the above applications are incorporated herein by reference.

INTRODUCTION

The present invention relates to methods for the production of sol-gel based matrixes as well as sol-gel based matrixes obtainable by such methods. The sol-gels of the present invention are useful for various purposes including use in sensors for measuring of pH, radiation, oxygen concentration etc. due to their high stability and porosity. Composites comprising the sol-gels of the present invention and a platform of microstructure area are also disclosed. Methods for preparing these composites or sensors are provided se well.

BACKGROUND OF THE INVENTION

First generation optical sensors are currently being introduced in biotechnological production platforms. The sensors are composed of five different units, excluding the fiber optical connectors: i) light source, ii) substrate, iii) matrix, iv) indicator dye components, and v) detector.[1-5]

Light sources and detectors are highly developed and is just a question of costs. The substrate has to be chosen based on the platform in which the sensing will take place, typically a glass or a polymer support is used. The key parameter regarding the substrate is that the matrix material must be able to be at least partly immobilized in or on the substrate.

The wish list for the matrix material is long: the matrix material should allow the analytes to pass through the film as unhindered as possible, it should encapsulate the sensor molecules, it should be transparent and have a low auto-fluorescence, and it has to be stable in biological media for extended periods of time. The indicator dye components may be either a single ratiometric pH responsive dye, or two dyes with similar properties. The latter is only possible if the physical stability of the matrix ensures that no dye is lost to the medium.

The benchmark in materials for optical sensors has been set in sensors, where fluorescein has been used as the indicator dye component[4-8] despite the poor photostability of fluorescein.[5] The critical parameters are the response time of the sensor, the leakage of the dye, the stability of the signal and the response to pH. While leakage of the highly water soluble fluorescein from the prior art optical sensors has not been completely removed,[9] other more lipophilic dyes have been successfully encapsulated in sol-gel matrices.[10, 11] However, even lipophilic dyes may be prone to leakage during long term use or in lipophlic/amphiphilic environments.

Preparation of organically modified silicates (OR-MOSILs) using alkyl and 3-glycidoxypropyl substituted trialkoxysilanes and various polymerization conditions have been reported previously in the scientific literature.[1, 12, 13] Leakage has been controlled either using apolar additives[11, 14] or by attaching the dyes to bulky macromolecules.[6, 7, 15, 16] It has been reported that Lewis acids can be a catalyst for polymerization of 3-glycidoxypropyltrialkoxysilanes, accelerating both the polyether and the polysiloxane formation.[12, 13, 17]

WO 2009/020259 discloses in example 2 a method in which 3-glycidoxypropyltrimethoxysilane (GPTMS), methyltriethoxysilane (MTES), ethanol (6.95 mM) and 35% HCl were mixed together and stirred at room temperature for three days to induce a condensation reaction. To the sol-gel solution thus prepared, 1 mM HPTS solution, which had been dissolved in ethanol was added to give a HPTS mixture solution. The HPTS mixture solution was evenly coated onto the bottom surface of wells of a microtiter plate to prepare a fluorescent sensing membrane that can be used for detection of carbon dioxide. The sol-gel solution comprising coated HPTS was dried at room temperature for five days and further dried at 70° C. for two days for improving a mechanical strength and surface smoothness. WO 2009/020259 uses HCl as the initiator and the indicator moiety (HPTS) is non-covalently attached to a silane.

WO 2004/077035 discloses a $CO_2$ sensor comprising a pH-indicator and a porous sol-gel matrix. The pH-indicator may be hydroxypyrene trisulfonate (HPTS) and immobilised in the sol-gel. The sol-gel may be prepared from the monomer ethyltriethoxysilane (ETEOS). In the specific method, two silanes are used (trimethylsilylpropane and triethoxysilane). However, none of the silanes suggested in the description contains an epoxy group. Furthermore, the indicator moiety is not covalently linked to a silane.

WO 12/032342 discloses a sensor comprising a sol-gel layer incorporating a phosphorescent material, such as ruthenium oxide ($RuO_2$). The sensor may be used for measuring the $O_2$ or the $H_2S$ concentration. Details on the monomers used in the sol-gel are not disclosed.

J. Mater. Chem. 2012, 22, 11720 shows a method in which two monomers (ETEOS and GPTMS) are used in the sol-gel. The monomers are separately reacted and methylimidazole is used to initiate the reaction of GPTMS. When the separately reacted monomers are mixed, the indicator moiety (HPTS) is added. Thus, a Lewis acid for initiating the reaction is not used and an indicator moiety (e.g. HPTS) is not covalently attached to a silane. Methods based on catalysis by methylimidazole may be inferior, as tests performed by the present inventors have shown that methylimidazole reacts and form fluorescent compounds, which are immobilized in the sol-gel.

It is the purpose of the present invention to improve the porosity of sol-gel materials for optical sensing, while at the same time maintaining a high physical stability and a low auto-fluorescence. A high porosity results in a short response time, which makes it possible to react on a change faster.

SUMMARY OF THE INVENTION

The present invention relates to a method for the production of a sol-gel based matrix comprising the steps of:
a) providing a first alkoxysilane of the general formula:
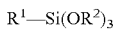
and a second alkoxysilane of the general formula:

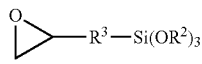

wherein

R¹ represents a straight or branched $C_1$-$C_6$ alkyl or $C_2$-$C_6$ alkenyl, a $C_3$-$C_6$ cycloalkyl, a $C_1$-$C_6$ aminoalkyl, a $C_1$-$C_6$ hydroxyalkyl, a $C_1$-$C_6$ cyanoalkyl, a phenyl, a group of the formula —Y—(X—Y)$_n$H, wherein Y independently is selected from straight or branched $C_1$-$C_6$ alkylene, X is a hetero atom or group selected among O, S, NH, and n is an integer of 1-5, or R¹ represents a $C_1$-$C_6$ alkyl substituted with a group Z, wherein Z independently is selected form the group comprising hydrogen, cyano, halogen, hydroxy, nitro, amide $C_1$-$C_{24}$-alkyl, $C_1$-$C_{24}$-haloalkyl, $C_2$-$C_{24}$-alkenyl, $C_2$-$C_{24}$-alkynyl, aryl, $C_1$-$C_{24}$-alkoxy, $C_1$-$C_{24}$-alkylsulfonyl, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester comprising a $C_1$-$C_6$ alkyl alcohol moiety, (carboxyl ester)amino comprising a $C_1$-$C_6$ alkyl alcohol moiety, (carboxyl ester)oxy comprising a $C_1$-$C_6$ alkyl alcohol moiety, sulfonyl, sulfonyloxy, thiol, thiocarbonyl, $C_1$-$C_{24}$-alkylthio, 5 or 6 membered heteroaryl, or a $C_3$-$C_7$ cycloalkyl;

R² independently represents a straight or branched $C_1$-$C_6$ alkyl; and

R³ represents a linker chosen from a group of the formula

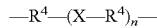
—R⁴—(X—R⁴)$_n$— wherein R⁴ independently is selected from straight or branched $C_2$-$C_6$ alkylene, $C_2$-$C_{24}$-haloalkylene, X is a hetero atom or group selected among O, S, NH, and n is an integer of 0-12, b) preparing a first sol-gel component by polymerisation of the first alkoxysilane in the presence of an acid catalyst, c) preparing a second sol-gel component by polymerisation of the second alkoxysilane in the presence of an Lewis acid catalyst, d) Mixing the first sol-gel component and the second sol-gel component for the preparation of a sol-gel based matrix.

It was discovered by the inventors that the use of a Lewis acid for the catalysis of the second sol-gel component did not result in the formation of fluorescent compounds or other by-products, as was the case for methylimidazole. Furthermore, the Lewis acid showed the added potential of being incorporated in the sol-gel, thus adding to the porosity.

In another aspect of the present invention an additional alkoxysilane is added to step b) and/or c), said additional alkoxysilane being of the formula:

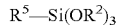
R⁵—Si(OR²)$_3$ wherein R² is as defined above and R⁵ represents a group having covalently attached an indicator or reference dye.

While the present invention may work well in many applications with an indicator dye or reference dye non-covalently attached to the silane scaffold matrix a more durable sol-gel based matrix may be obtained by attaching the indicator or reference dye covalently to the matrix. A more stable product may collect reliable data for prolonged time. The added physical stability may further broaden the application of the sensor incorporating the sol-gel based matrix to applications in which the indicator or reference dye may otherwise easily leak to the media.

The indicator dye or the reference dye may be attached to the silane matrix in a variety of ways. In a certain embodiment R⁵ is of the general formula

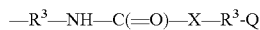
—R³—NH—C(=O)—X—R³-Q wherein R³ is as defined above and independently selected, and Q represents an indicator and/or a reference dye.

The reference dye and/or the indicator dye can be selected from a variety of possibilities well known for the person skilled in the art. According to a certain aspect of the present invention Q is an indicator dye derived from 8-hydroxypyrene-1,3,6-trisulfonic acid (HPTS), fluorescein, or rhodamine B.

The type of reference dye is not particularly limited to a certain class of compounds. Thus, in an embodiment of the present invention Q in the above formula is a reference dye derived from triangulenium compounds, acridinium compounds, ruthenium doped sol-gel particles, ruthenium-based compounds with α-diimine ligands, porphorin with Pt or Pd as the central metal atom, Ru(bpy)$_2$(dpp)Cl$_2$, Ru(bpy)$_3$Cl$_2$, a lanthanide containing complex, or polymeric metal containing structure.

According to the present invention a Lewis acid is used in the polymerization of the second sol-gel component. Definitions of Lewis acids may vary from textbook to textbook. The IUPAC definition is "a molecular entity (and the corresponding chemical species) that is an electron-pair acceptor and therefore able to react with a Lewis base to form a Lewis adduct, by sharing the electron pair furnished by the Lewis base". Usually, the Lewis base is ⁻OH present in the media. In a certain embodiment of the present invention a Lewis acid is a triagonal planar species, such as BF$_3$ or AlCl$_3$. Specific examples of Lewis acids according to the present invention include TiCl$_4$, AlCl$_3$, and BF$_3$, or solvates or etherates thereof.

The additional alkoxysilane may be added at any suitable point in time during the method. In a preferred aspect, the additional alkoxysilane is added to first sol-gel component, the second sol-gel component or both during the preparation.

When an indicator dye as well as a reference dye is present it is preferred that either the reference dye or the indicator dye is added to the first sol-gel component of step b) and the other dye is added to the second sol-gel component of step c).

The first alkoxysilane may be selected in accordance with the formula indicated above. Specifically, the first alkoxysilane is selected among ethyltriethoxysilane (ETEOS), methyltriethoxysilane (MTEOS), propyltriethoxysilane (PrTEOS), n-octyltriethoxysilane (n-octyl TEOS), methyltrimethoxysilane (MTMOS), aminopropyltrimethoxysilane (APTMOS), phenyltriethoxysilane (PhTEOS), and phenyl trimethoxysilane (PhTMOS). In certain matrixes a first silane with a less bulky side groups may be preferred to ensure high response times. Examples of such preferred first alkoxysilanes are ETEOS, MTEOS, PrTEOS, and MTMOS.

The second alkoxysilane may be selected in accordance with the formula indicated above. Specifically, second alkoxysilane is selected among 3-glycidoxypropyltrimethoxysilane (GPTMS).

The method described herein produces a sol-gel based matrix. The sol-gel based matrix so produced is also part of the present invention.

The relative amount of the individual components of the sol-gel based matrix may be adjusted in accordance with the need and desired properties of the final product. In a certain aspect the amount in mole of first alkoxysilane to second alkoxysilane is in the range of 10:1 to 1:10. Suitably, the amount of the first alkoxysilane to second alkoxysilane is in the range of 5:1 to 1:5, such as 2:1 to 1:2, preferable around 1:1.

In one aspect, the invention relates to a composite comprising a layer of sol-gel based matrix and a platform comprising a microstructure area, wherein the sol-gel based matrix is attached to the microstructure area. In one embodiment, the composite comprises a sol-gel based matrix according to the invention.

The composite of the invention provides a fast response time for the detection of analytes. The response of the composite may be detectable by detecting light or other electromagnetic radiation emitted by the sol-gel matrix, e.g. fluorescence and/or phosphorescence, and/or the like.

The platform may comprise a plurality of microstructures, such as 2, 10, 50, 100, 1000, or more microstructures. The microstructure may be arranged in an array measuring various analytes and concentrations thereof.

For the purpose of the present description, the term microstructure area refers to a structure having a plurality of micrometer-scale pillars. The plurality of micrometer-scale pillars may be depressions and/or protrusions of a predetermined cross-sectional geometry, e.g. cylindrical or conical pillars. The microstructure may have a shape having an extent in at least one dimension, e.g. in two or even all three dimensions, between 0.1 µm and 50 mm, e.g. between 1 and 20 mm, preferable between 5 and 10 mm.

The pillars may be cylindrical, cubic, or any other form. The pillars may be arranged in a pattern, e.g. a regular pattern, in a square or hexagonal grid. However, a random pattern of pillars may be used as well. The pillars may have any size and shape. The pillars may be between 0.1 µm and 500 µm, preferably between 5 and 100 µm, more preferable between 10 and 40 µm in height.

The distance or length between each pillar may be between 0.1 µm and 500 µm, preferably between 5 and 100 µm, more preferable between 10 and 40 µm. The width or diameter of the pillars may be between 2 and 100 µm, more preferable between 5 and 40 µm.

In a preferred embodiment the distance between each pillar is between 5 and 40 µm, the height of the pillars are between 10 and 40 µm and the width of each pillar is between 5 and 40 µm. The pillars are preferably arranged in a hexagonal geometry. An example of such preferred arrangement and geometry of the pillars in the microstructure in the platform area is shown in FIG. 10. The advantage of this embodiment is that it allows single step manufacturing of blown molded flask and injection molded container parts with one or more microstructures and at the same time is suited for attaching the sol-gel based matrix to the microstructure because it is an optimal compromise between the rheology of the plast/glass of the container and the ability to form a strong attachment with the sol-gel based matrix.

The microstructure may comprise a plurality of pillars in which the pillars, depressions and/or protrusions have different heights. The distance between the pillars, depressions and/or protrusions may be different.

The microstructure may be made of any suitable material such as a polymer, a plastic, glass, etc. Examples of suitable materials include inorganic materials, such as silicon, silicon oxides, silicon nitrides, III-V materials, such as, e.g., GaAs, AlAs, etc. Further examples of suitable materials include organic materials, such as, but not limited to, SU-8, polymethylmethacrylate (PMMA), polycarbonate (PC), polystyrene (PS), TOPAS(R) (cyclic olefin copolymer), organically modified ceramics (ORMOCER(R)). The material may be optically transparent or reflective at the used wavelengths of light or other electromagnetic radiation.

In one embodiment, the microstructure area comprises a plurality of pillars having a height between 0.1 µm and 500 µm and a distance between each pillar between 0.1 µm and 500 µm. The microstructure may also be applied to a curved surface. However, irrespective of whether the surface is curved or not, the shape of the pillars forming the microstructure area may be designed such that the microstructure area also improves or even optimizes the extraction of the light from a deposited sol-gel based matrix material during use as an optical sensor. For example, when the microstructure is an multitude of pillars that have a truncated-conical shape, the light emitted from a deposited sensor material may be directed to the optical sensing element through reflections on the inner surfaces of the pillar.

In one embodiment, the layer of the sol-gel based matrix has a thickness smaller than the height of the microstructure or the height of the pillars. Thus the microstructure or the pillars of the microsture penetrates the layer of the sol-gel based matrix, thereby providing stability to the sol-gel based matrix. Thus, the attachment of the sol-gel based matrix to the microstructure is improved.

In another embodiment, the composite comprises one or more sol-gel based matrixes comprising indicator or reference dyes. If the composites of the invention comprise different reference and indicators dyes, it will be possible to monitor one or more analytes and/or contractions thereof simultaneously. The use of the composites of the invention reduces the amount of space required for the monitoring.

In yet another embodiment, the invention relates to an array of sol-gel based matrixes attached to different areas on the microstructure area. In yet another embodiment, the plurality of sol-gel based matrixes includes at least two sol-gel based matrixes having different indicator or reference dyes.

A plurality of separate platform areas, e.g. a plurality of of sol-gel based matrixes on respective of sol-gel based matrixes areas, may be provided; in particular the plurality of sol-gel based matrixes may include at least two of sol-gel based matrixes having different thickness of the respective layer of the sol-gel based matrixes. Hence, different properties, e.g. sensitivity, may be provided. Further, different layers of sol-gel based matrixes may be obtained by providing variations in height/spacing profile of the microstructure.

This is particularly suitable for providing of sol-gel based matrixes on an inside surface of a container, e.g. a container for accommodating a fluid, e.g. a bottle, a tube, a flask, a bag, a microtitre plate, and/or the like. The surface may be planar or have a curvature in one or more directions. The deposited of sol-gel based matrixes may thus be used to sense e.g. analytes or other properties of a medium (e.g. a fluid) in contact with the surface, e.g. a medium inside a container or or laboratory consumable. In particular, the sol-gel based matrixes may be read by detecting light emitted from the of sol-gel based matrixes responsive to the detected property. The light emission may be detected through the wall of a container by a detector placed outside the container or or laboratory consumable.

In yet another embodiment, platform of the composite is an inner surface of a container or conduit for transporting a fluid. In yet another embodiment, the container comprises an opening and cylindrical or tapered sides, and is closed opposite to the opening. In yet another embodiment, the platform is an inner surface of a disposable container for transporting a fluid.

The composite may amongst other without being limited be deposited in and/or constitute a part of open or closed containers, or laboratory vessels, dedicated sensing equipments and laboratory consumables to act as a build-in sensor for analytes such as pH, dissolved oxygen (DO), conductivity, etc.

The composite may be deposited and constitute a part of open or closed containers, or laboratory vessels to yield a sensor spot, which may be circular or take any other form. The amount deposited may be 1 ul, 10 ul, 100 ul or even more. Any number of sensor spots can be deposited in a piece of equipment, consumable or vessel. The size of the spot may be 100 um$^2$, 1 mm$^2$, 10 mm$^2$, 100 mm$^2$, 1 cm$^2$, 10 cm$^2$, 100 cm$^2$ or even more.

The container or laboratory consumable may be made of glass, polystyrene, polycarbonate or any polymer or composite material transparent to light, preferable green and red light (450 nm to 800 nm).

In one aspect, the invention relates to the use of a composite according to the invention for monitoring of a bioculture. The environment and development of the bioculture may be followed, periodically or continuously, e.g. by detecting light emitted from the composite or sensor.

Thus, the sol-gel based matrixes and composites of the invention may be used as integrated sensors or propes, thereby reducing the risk of contamination as these can be read from the outside of the container and/or laboratory vessels.

In one aspect, the invention relates to a method for the preparation of a composite, comprising
  providing a platform with a predetermined microstructure, and
  depositing a layer of sol-gel based matrix on at least a part of the microstructured area.

Methods for deposition of sensor material, such as a sol-gel based matrix, on a homogeneous layer in a well-defined region of a surface are well known in the art, Quéré D 2008, Annu. Rev. Mater. Res. 38 71-99. A drop of liquid material that is deposited on the microstructured area will spread, guided by the structures of the pillars, to homogeneously fill the volume between the pillars.

Generally, a sol-gel process, also known as chemical solution deposition, is a wet-chemical technique suitable for the fabrication of materials, e.g. a metal oxide, or glass, starting from a chemical solution acting as a precursor for an integrated network, or gel, of discrete particles or network polymers. The process typically includes the removal of liquid after deposition of the precursor on the surface, e.g. by sedimentation and removal of the remaining solvent, by drying, and/or the like. Afterwards, a thermal treatment, or firing process, may be employed.

Microstructuring of e.g. the inside of blow-molded plastic containers may be performed using step-and-stamp imprint lithography (Haatainen T and Ahopelto J 2003 *Phys. Scr.* 67 357), and for plastic components produced by injection molding, microstructures can be integrated directly in the mold (Utko P, Persson F, Kristensen A and Larsen N B 2011 *Lab Chip* 11 303-8). Both of these fabrication methods are suited for large-scale industrial production.

Spreading of the liquid is governed by the geometry of the microstructures and the thickness of the deposited film is determined by the height of the pillars and is thus independent of the volume of the deposited drop. This enables easy and reproducible deposits of spots of the sol-gel based matrix of precise thickness to be made surfaces, such as metallic and plastic surfaces.

Spreading of the sol-gel based matrix enables direct, controlled deposition of spots of the sensor material inside containers, and it simplifies the fabrication of optical sensors in disposable lab ware.

The term immobilising is intended to refer to any process for causing deposited layer to remain fixed as an integral layer covering and attached to at least a portion of the deposition area. The immobilising or fixation of the deposited sol-gel based matrix may be performed by a variety of techniques, e.g. by curing, hardening the deposited liquid, by evaporation of a solvent, by a sedimentation process, by covering the deposited sol-gel based matrix by a sealing layer, e.g. a foil, membrane etc. and/or a combination of the above. For example, the deposited sol-gel based matrix may be immobilized on the surface by solvent evaporation, by cross-linking due light exposure, exposure by other forms of electromagnetic radiation, and/or by thermal treatment, and/or by any other suitable curing process. Materials which remain liquid after deposition on the microstructures are also a possibility; such materials may be immobilized by depositing a cover layer, e.g. a membrane, on top of the deposited sol-gel based matrix. Hence, the process results in a composite layered product in which the microstructure area and a layer of deposited sol-gel based matrix are efficiently bonded to each other.

In some embodiments, e.g. due to the removal of the liquid, e.g. by solvent evaporation, the immobilising process may cause a volume reduction of the immobilised sol-gel based matrix compared to the initially deposited volume. This may result in the immobilised sol-gel based matrix having a local thickness, measured in the spaces between protrusions of the microstructure, smaller than the height of the microstructure. This may also result in a convex upper surface of the immobilised deposited sensor material. In that case the optical path through the film on vertical side walls is much larger than the thickness of the film that an analyte has to diffuse through, and a larger surface is achieved, thus reducing the response time of the sensor.

In one embodiment of the invention, at least a part of the sol-gel based matrix is immobilised resulting in an immobilised layer of sol-gel based matrix attached to the surface of the microstructure area. In another embodiment of the invention, the immobilised layer of sol-gel based matrix has a thickness smaller than the height of the microstructure. In yet another embodiment of the invention, the microstructurea area is prepared by a process chosen from injection molding, hot embossing, laser microstructuring, micromachining, chemical etching, photoresist layer structuring.

BRIEF DESCRIPTION OF THE DRAWINGS

FIG. 4 shows the ratiometric responses.

FIG. 5 shows the emission spectra of the sensors in action.

FIG. 6 shows the response times of the pH active dye DAOTA-2.

DETAILED DESCRIPTION OF THE INVENTION

Figure 1:
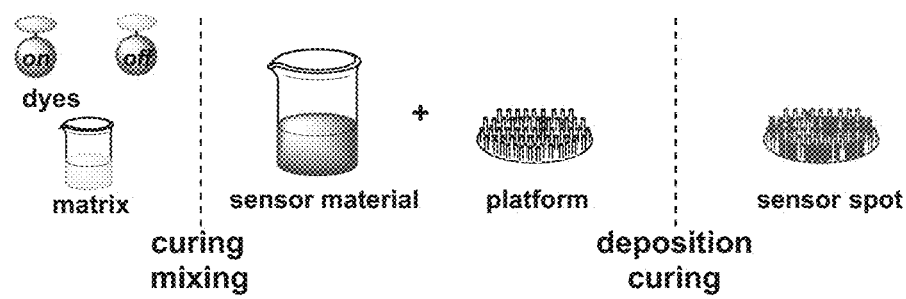
FIG. 1 shows the general preparation steps for deposition of sensor material on a substrate.

The sol-gel based matrix is usually deposited on a substrate as a part of a sensor. The substrate is generally selected to optimise the ability of the sol-gel to form an immobilized attachment to the substrate. Suitable substrates include glass, plastics, ceramics, and polymers. Suitable polymer substrates include polycarbonates, acrylics such as poly(methyl methacrylate), acrylonitrile-butadiene-styrene copolymer, polyvinylchloride, polyethylene, polypropylene, polystyrene, polyurethanes, silicones, and vinylidene fluoride-hexafluoropropylene copolymer.

The first sol-gel component is prepared by polymerisation of the first alkoxysilane defined above in the presence of an acid catalyst. The acid catalyst may be any suitable acid, such as an inorganic or organic acid. Suitable inorganic acids include hydrochloric acid (HCl), nitric acid ($HNO_3$), phosphoric acid ($H_3PO_4$), sulphuric acid ($H_2SO_4$), hydrofluoric acid (HF), hydrobromic acid (HBr) and perchloric acid ($HClO_4$). A preferred inorganic acid is hydrochloric acid. Suitable organic acids include lactic acid, acetic acid, formic acid, citric acid, oxalic acid, and malic acid. Furthermore, the acid catalyst may be any combination of the above compounds.

To be suitable, the acid chosen must be able to hydrolyse the first alkoxysilane under the acidic conditions. The hydrolysis initiates the polymeric condensation reaction upon formation of a polymer silicon oxide network.

The procedure for the preparation of the first sol-gel component generally include that the first alkoxysilane is dissolved in an organic solvent, usually an alcohol like ethanol prior to the addition of the acid catalyst. The amounts in mole of acid are generally at the same level or lower as the molar amount of the first alkoxysilane. The mixture of first alkoxysilane, organic solvent and acid catalyst is left until the reaction is completed. The reaction time may be several days.

The second sol-gel component is prepared by either dissolving the second alkoxysilane in a solvent before the addition of the Lewis acid catalyst or by mixing the alkoxysilane and the Lewis acid and then adding the solvent. The molar amount of Lewis acid catalyst is generally lower than the molar amount of the second alkoxysilane. In a preferred embodiment the molar amount of Lewis acid to second alkoxysilane is 1:2, such as 1:3, preferably 1:4. The solvent is usually an alcohol like ethanol but may be chosen among various solvents assumed by the skilled person to be inert under the conditions.

The Lewis acid is believed to attack the epoxy ring of the second alkoxysilane whereby a secondary carbocation is formed. This intermediate carbocation can then react with another molecule in the polymerisation process. The amount and the type of second alkoxysilane should be chosen so as to be able to participate in the intended chemical reaction within a reasonable time. The formation of the second sol-gel component normally proceeds much faster than the formation of the first sol-gel component. A typical reaction time for the second sol-gel component is between 10 min and 3 hours. After the reaction the second sol-gel component is typically allowed to rest for a few hours.

After the two sol-gel components have been prepared separately, they are mixed. Typically, the molar amount of the first sol-gel component to the second sol-gel component is in the range of 5:1 to 1:5, such as 3:1 to 1:3, typically 2:1 to 1:2, and suitably approximately 1:1.

If the sol-gel matrix is used for sensing, an indicator and/or reference dye may be incorporated in to the matrix by a number of methods to obtain either a non-covalent or a covalent attachment. If a non-covalent attachment is used it is preferred to anchor the dye in some way to the matrix to avoid excessive leakage. A preferred anchoring method is the so-called lipophilic entrapment, according to which the dye core is provided with one or more lipophilic linkers. The lipophilic linkers will engage with the lipophilic environment of the network formed by the sol-gel components and thereby retard the leakage. In a preferred method the dye core provided with one or more lipophilic linkers is added either to one or both of the sol-gel components or to the mixture of the first and the second sol-gel component. To ensure a sufficient maturation of the mixture it may be kept for 1 hour to 7 days before it is deposited on the substrate and cured.

A covalent attachment of the dye is possible by linking the dye to one of the monomers before polymerisation. In a preferred method, an additional alkoxysilane is prepared as a derivative of the first alkoxysilane by attaching the dye thereto. The additional alkoxysilane may be incorporated into either the first sol-gel component or the second sol-gel component. In a preferred aspect the first or second alkoxysilane is allowed to polymerise a short time, such as at least 15 minutes, before the further alkoxysilane is added to avoid end positioning.

The mixture of the first sol-gel component and the second sol-gel component may be allowed to mature before the deposition on a suitable substrate. The substrate is generally transparent at the wavelength used for monitoring the emitted light. The amount of the mixture used for deposition varies in dependence of the purpose and geometry of the sensor. In a certain aspect the amount is 100 µl or less, such as 50 µl or less, suitably 20 µl or less. The deposition may be referred to herein as a "spot".

The addition of the mixture to the substrate may be allowed deliberately to solidify or the added amount of mixture may be spread on the substrate to form a film with an essentially uniform thickness. After the deposition of the mixture on the substrate it is cured. The curing may be performed in a number of ways, including heating at elevated temperatures so as to form a solid film attached to the substrate. The temperature of the curing is suitably 70° C. or above, such as 90° C. or above, and suitably 100° C. or above. Usually, the curing temperature does not exceed 150° C. to avoid degradation of the materials, i.e. to maintain the porous three dimensional polymer networks, which allow for fast diffusion of the analyte, such as a proton. The relatively unhindered diffusion of the analyte in the porous network is believed to be the reason for the observed fast response time.

The research reported herein suggests that covalent attachment of the dye to the polymer network is preferred when a long-time stability is of importance. Even when the dyes are provided with lipophilic linkers to retard the leakage from the film, the leakage is still too high for a product stabile over a longer time period to be obtained. For short-time use, such as in non-reusable sensors, non-covalently attached dyes may be acceptable.

Figure 9:
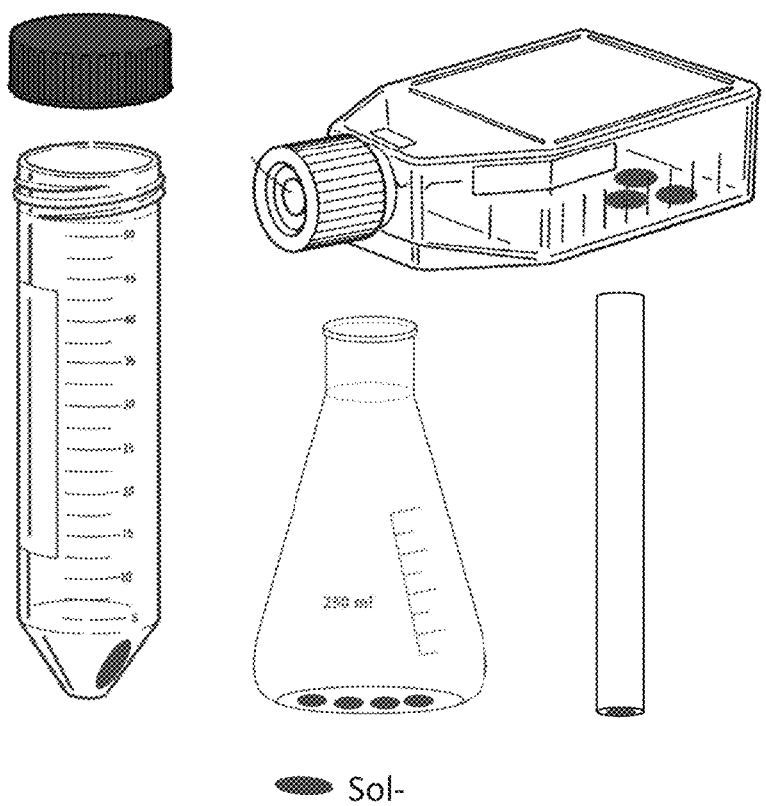
FIG. 9. Example of laboratory consumables comprising a sol-gel matrix according to the invention.
Figure 10:
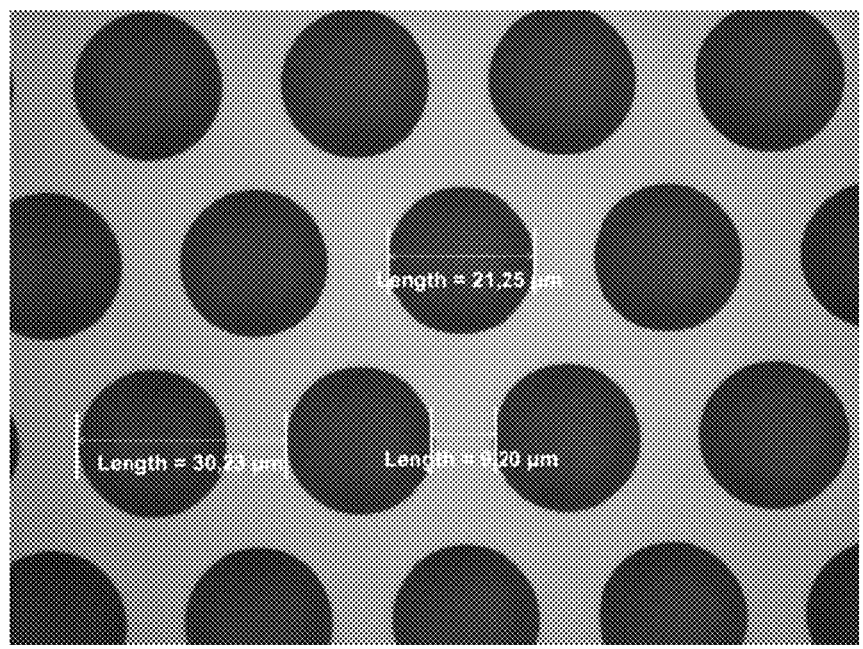
FIG. 10 shows a preferred arrangement and geometry of the microstructure in the platform area.

An aspect of the invention relates to the manufacturing of a container or laboratory equipment with a composite, i.e. a container or laboratory equipment respectively comprising one or more platforms. Particularly suited laboratory equipment is ehrlenmeyer flasks, beaker glasses, tissue culture flasks, tissue culture dishes, tissue culture plates and storage systems. Examples of laborative equipments comprising the composite of the invention are shown on FIG. 9.

EXAMPLES

Methods and Materials

Compounds were used as received. Sol-gel monomers were purchased from Sigma-Aldrich. Sol-gel catalysts were purchased from Sigma-Aldrich and used as recieved. Solvents used were analytical or HPLC grade. An electronically controlled oven was used to cure the ORMOSIL thin-films.

Synthesis

The synthesis of compounds $1.BF_4$ and $2.PF_6$ are reported elsewhere.[18]

General Preparation of Tetramethoxyamino-Acridinium (TMAAcr)

2 (162 mg, 0.23 mmol) was dissolved in 15 ml acetonitrile and n-octylamine (26 ml, 0.14 mmol) was added to the solution. The reaction mixture was heated to slight reflux temperature and stirred in 5 h. The reaction mixture was allowed to cool down when the color of the mixture had changed from blue to red-brown and MALDI-TOF analysis indicated that a mass corresponding to that of the starting material was not present any more. The reaction mixture was washed with heptane (3×50 ml). The crude product was isolated by evaporation and recrystallized from ethanol, and the product was washed with ether and heptane several times. The product was isolated as a red-purple powder, which was metallic-green when filtered.

General Approach to Activate TMAAcr for Covalent Attachment:

TMAAcr (100 mg, 0.11 mmol) was dissolved in 20 ml acetonitrile and then triethoxy(3-isocyanatopropyl)silane (1.1 ml, 0.45 mmol) was added dropwise using a syringe at room temperature. The mixture was stirred for 1 h, when MALDI-TOF analysis indicated that 9 was not present. The reaction mixture was washed with heptane (3×50 ml) and then the acetonitrile phase was mixed with a 0.2 M $KPF_6$ solution. The slurry was stirred for 20 min and then gently filtered. The precipitate was washed with water several times. The product was dissolved in dichloromethane through the filter and the non-dissolved solid in the filter was discarded. The product is collected by removal of the solvent yielding metallic-green flakes.

General Preparation of Dimethoxyquinacridinium (DMQA):

A primary amine (20 eq, 40 mmol) was added to a solution of $DMB_3C.BF_4$[19] in NMP (1.0 g, 2 mmol in 8 mL). The solution was warmed to 140° C. for 10-20 minutes (the degree of reaction is followed by MALDI-TOF mass spectroscopy). After cooling to RT the reaction mixture was poured on to 0.2 M $KPF_4$(aq) (200 mL). The precipitate was collected, washed and dried. The crude can be recrystallized from methanol, reprecipitated from dichloromethane with ethylacetate or reprecipitated from acetonitrile with ether depending on the how lipophile the side chains are.

General Approach to Activate DMQA for Covalent Attachment:

DMAQ (70 mg, 0.143 mmol) was dissolved in 8 ml anhydrous acetonitrile and then 3-(triethoxysilane)propyl isocyanate (cold, 100 ul, d=0.999 g/ml, 0.404 mmol) was added. The flask was fitted with a stopper and stirred at room temperature for 4 h. After 4 h MALDI-TOF analysis indicated that the reaction mixture only contained starting material. Then excess of isocyanate (1 ml) was added together with approx. 1 ml of triethylamine. The mixture was heated to 65° C. and stirred for 1.5 h. Then MALDI-TOF analysis indicated that the reaction mixture contained a compound with a mass of 649 m/z, which is the mass of the desired product and no mass corresponding to that of the starting material was present. The reaction mixture was washed (still warm) with heptane (2×50 ml) and then dried over $MgSO_4$ for 10 min. The solvent was removed by evaporation at 50° C. in vacuum and the crude product was dissolved in a minimum of $CH_2Cl_2$ and then diethyl ether (200 ml) was added and a green precipitate was allowed to form. The dark product was collected and dried in vacuum over KOH over night.

Spectroscopy

Emission spectroscopy was performed in front-face set-up for sensor spot samples and in a conventional L-shape set-up for measurements in solution. A Perkin-Elmer LS50B and a Horiba Fluorolog 3 were used interchangeably. Intensity based sensor measurements were only performed on the LS50B platform. Fluorescence lifetime based sensor measurements were only performed on the Fluorolog 3. Absorption spectroscopy was performed on a Perkin Elmer Lambda 1050, with integrating sphere (for sensor spots) and with a 3-detector module for solution samples.

Sol-Gel Preparation

The procedure includes preparation of two separate gel components of the organic modified silanes: Ethyltriethoxysilane (ETEOS) or a similar alkyl or aryl trialkoxy silane (XTEOS) and 3-(glycidoxy)propyltrimethoxysilane (GPTMS). All the different preparations and combinations are compiled in table 1, and the detailed procedures are as follows.

TABLE 1

The different compositions of sol-gels tested in this work; variations can be seen in the alkyltrialkoxy silane part, the Lewis acid, and the dye additives. The pKa of the resulting sensor is included.

| Entry | Monomer 1 | Monomer 2 | Catalyst | Dye 1 | Dye 2 | pKa |
|---|---|---|---|---|---|---|
| 1 | GPTMS | ETEOS | $BF_3$ | TMAAcr-1 | — | 3.8 |
| 2 | GPTMS | ETEOS | $BF_3$ | TMARh | — | 1.1 |
| 3 | GPTMS | ETEOS[1] | $BF_3$ | TMAAcr-3 | — | 2.6 |
| 4 | GPTMS | ETEOS[2] | $BF_3$ | TMAAcr-3 | — | 3.1 |
| 5 | GPTMS | ETEOS | $BF_3$ | TMAAcr-4 | DMQA-1 | 4.9 |
| 6 | GPTMS | ETEOS[1] | $BF_3$ | TMAAcr-6 | DMQA-1 | 4.8 |
| 7 | GPTMS | ETEOS | $BF_3$ | DAOTA-1 | DMQA-2 | 6.5 |
| 8 | GPTMS | ETEOS | $BF_3$ | DAOTA-2 | DMQA-2 | 6.5 |
| 9 | GPTMS | PrTEOS | $BF_3$ | DAOTA-2 | DMQA-2 | 6.5 |
| 10 | GPTMS | PhTEOS | $BF_3$ | DAOTA-2 | DMQA-2 | 6.7 |

TABLE 1-continued

The different compositions of sol-gels tested in this work; variations can be seen in the alkyltrialkoxy silane part, the Lewis acid, and the dye additives. The pKa of the resulting sensor is included.

| Entry | Mono- mer 1 | Mono- mer 2 | Catalyst | Dye 1 | Dye 2 | pKa |
|---|---|---|---|---|---|---|
| 11 | GPTMS | ETEOS | TiCl$_4$ | DAOTA-2 | DMQA-2 | — |
| 12 | GPTMS | ETEOS | AlCl$_3$ | DAOTA-2 | DMQA-2 | — |

[1]Dye 6 pre-mixed with ETEOS component,
[2]Dye 6 pre-mixed with GPTMS component.

ETEOS

The ETEOS gel component is prepared from polymerization of the silicon network under acidic conditions. ETEOS is hydrolysed under acidic conditions, which initiates a polymeric condensation reaction upon formation of a polymer silicon oxide network. The presented procedure is an equivalent to the procedure reported by Wencel et al.[10,11]

Procedure for preparation of ETEOS gel component: 5 ml ETEOS (0.02 mol) is dissolved in 8 ml absolute ethanol (0.14 mol) upon stirring. Hereafter, 1.6 ml of 0.1 M HCl solution (0.16 mmol) is added dropwise. This mixture is then left on a stirring table for a minimum of 7 days to allow the polymerization process to proceed.

GPTMS Gel Component.

The GPTMS gel component is prepared from polymerization of the organic linker using a Lewis acid as initiator. In this procedure we use boron trifluoride diethyletherate as the Lewis acid. The Lewis acid attacks the epoxy ring that allows for ring opening of the epoxy ring upon formation of a secondary carbocation. This intermediate carbocation can then react with another GPTMS molecule, initiating a polymerization reaction. Due to the acidic environment a polymerization of the silicon network equivalent to that described for the ETEOS component will proceed alongside.

Procedure for preparation of GPTMS gel component: 6 ml of GPTMS (0.027 mol) is mixed with 11 ml of absolute ethanol (0.19 mol) upon stirring. Then 0.75 ml of cold borontrifluoride diethyletherat (BF$_3$.O(CH$_2$CH$_3$)$_2$, 5.8 mmol) is added dropwise. The mixture is left with stirring for 30 min in a sealed container until the temperature of the mixture has dropped to room temperature. After 30 min 2 ml of MilliQ water (0.11 mol) is added to the solution. The resulting mixture was left with stirring for 4 h.

When the two gel components have been prepared they are mixed in 1:1 molar ratio and left for a minimum of 3 days to allow the networks to mix. This is referred to as the GPTMS-ETEOS mixture.

GPTMS-ETEOS Mixture

When the GPTMS and ETEOS components have been prepared they are mixed to obtain a 1:1 molar ratio (1.1 ml GPTMS+1 ml ETEOS) and the dyes are added in order to obtain a concentration of approx. 0.1 mM. The resulting mixture is then allowed to further mix for a minimum of 3 days.

The GPTMS-ETEOS mixture with the dye entrapped can now be deposited onto a glass or plastic surface. When deposited it has to be cured at 110 degrees for 3-4 h. The result is a porous and transparent matrix.

XTEOS Variations

A procedure analogous to that for the ETEOS Gel component described above used to make XTEOS gel components, with x=Pr and Ph.

Preparation of XTEOS Gel Components

X=Phenyl (Ph): Phenyltriethoxyilane (PhTEOS, 10 ml, M=240.14 g/mol, d=0.996 g/ml, 0.041 mol) and absolute ethanol (15 ml, d=0.789 g/ml, 0.26 mol) was mixed and the freshly prepared 0.1 M HCl solution (2.8 ml, 0.28 mmol) was added. The solution was stirred for 15 min in the sealed vial, and then left at a vibration table for 20 days in the dark at room temperature.

X=Propyl (Pr): Propyltriethoxyilane (PrTEOS, 10 ml, M=206.13 g/mol, d=0.892 g/ml, 0.043 mmol) and absolute ethanol (16 ml, d=0.789 g/ml, 0.27 mol) was mixed and then freshly prepared 0.1 M HCl solution (3.2 ml, 0.32 mmol) was added. The solution was stirred for 15 min in the sealed vial, and then left at a vibration table for 20 days in the dark at room temperature.

Lipophilic Entrapment

In the lipophilic entrapment method the dyes in entrapped in the GPTMS-ETEOS network requires that the dye has one or several lipophilic linker(s) attached to the dye to prevent leakage from the resulting matrix material.

General Procedure for Lipophilic Entrapment of Dyes

The ETEOS and GPTMS gel components are prepared and mixed as described above with the addition of the dye such that a final concentration of 0.1 mM is obtained. The resulting GPTMS-ETEOS-dye mixture is then left at a stirring table for at least 3 days before deposition and curing at 110° C. for 3-4 hours.

Covalent Method:

This procedure requires that the dye has been activated by linking to a trialkoxysilane group that can mix into the silicon network of either the ETEOS or GPTMS gels.

General Procedure for Covalent Entrapment of Dyes into the GPTMS-ETEOS Matrix

The ETEOS and GPTMS gel components are prepared and mixed as described above, with the exception that the silane functionalized dye is mixed into the either the ETEOS or the GPTMS gel component after 1 h after mixing of the materials described to mix the ETEOS or the GPTMS gel components. The GPTMS and ETEOS components are left for polymerization reaction time described in the general procedure. The two components are then mixed in the described 1:1 molar ratio and left at a stirring table for no less than 3 days. The dye should be added in an amount so that a final concentration of 0.1 mM of dye is obtained in the final GPTMS-ETEOS mixture. The resulting GPTMS-ETEOS-dye mixture is then deposited and cured at 110° C. for 3-4 hours.

Fabrication of Sensor-Spots

The sensor spots were drop coated on a glass or polycarbonate substrate and then cured. The substrate material appears to be inconsequential as long as thin films can be prepared. For comparison sensor spots were prepared from direct incorporation of the dyes in PVA (from 10% w/w solutions in water) which were subsequently drop coated on glass. PEG-DA hydrogel with dye entrapped was prepared by mixing PEG-DA (M$_n$=700) and ethanol in a 1:1 v/v ratio and then the dye was added to obtain 1 mM. Then a catalytic amount of a solution of 2,2'-azobis(2-methylpropionitrile) in CH$_2$Cl$_2$ (25 mg/ml) was added. The mixture was spread out on a petri dish, the dish was equipped with a glass lid, and the mixture was baked in the oven at 110° C. for 1 h. A thin piece of the resulting hydrogel was immobilized on a clean glass slide using double-sided tape and the regular tape.

Titrations

To perform titrations rapidly a set-up employing an epifluorescence microscopy equipped with a halogen light source and an Ocean Optics spectrometer for detection. The sensor spot was attached to a homemade holder, which kept the spot in place in a large chamber filled with water, where pH was externally monitored with a pH meter. Alternatively the sensor spot was affixed on the wall of a cuvette and the titration was performed in a Perkin Elmer LS50B, controlling the pH between measurements.

Stability Testing

The photostability was followed by constant illumination of the sensor spot with wavelength selected light from a xenon lamp. The physical stability was tested by immersing the sensor spot in low or high pH aqueous solution, and monitoring the fluorescence from the solution.

Response Analysis

The signal from the sensor is monitored after inducing a significant (more than 4 pH units) jump in pH. The time it takes to obtain a full (100%) and partial (90%) response, compared to the equilibrium signal is recorded.

FIG. 1 shows the general preparation of sensor spots.

Results

The tested sensors are prepared as illustrated in FIG. 1, on glass and polycarbonate substrates. The five components are mixed in a fashion that allows for the formation of a porous covalently linked 3D polymer network, which allows for fast diffusion of protons.

Scheme 2 shows the structure of the pH-responsive and the reference dyes used in this study. The pKa values of the resulting sol-gel based sensors are compiled in table 1. Cursory inspections of the structures, which are physically immobilized in the sol-gel show that a long alkyl chain is required to prevent leakage, while the molecules covalently linked to the matrix can have either a long or a short linker.

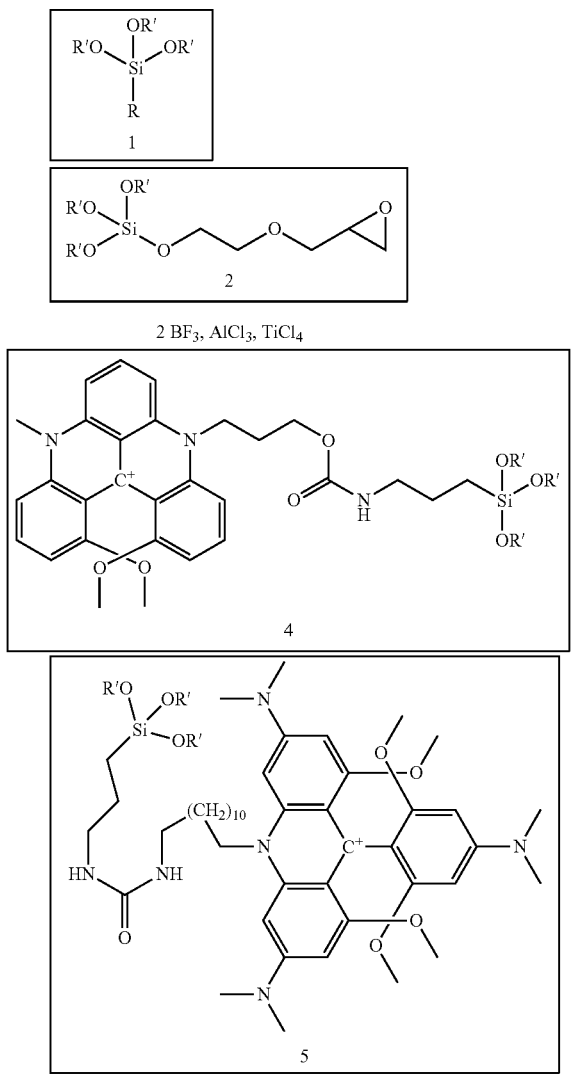

Scheme 1: Above is shown the five components used to form the sol-gel sensor material in the present example.

1: Alkyl trialkoxy silane
2: 3-(glycidoxy)propyltrialkoxysilane
3: Lewis acid
4: Dye-1-trialkoxy-silane
5: Dye-2-trialkoxy-silane

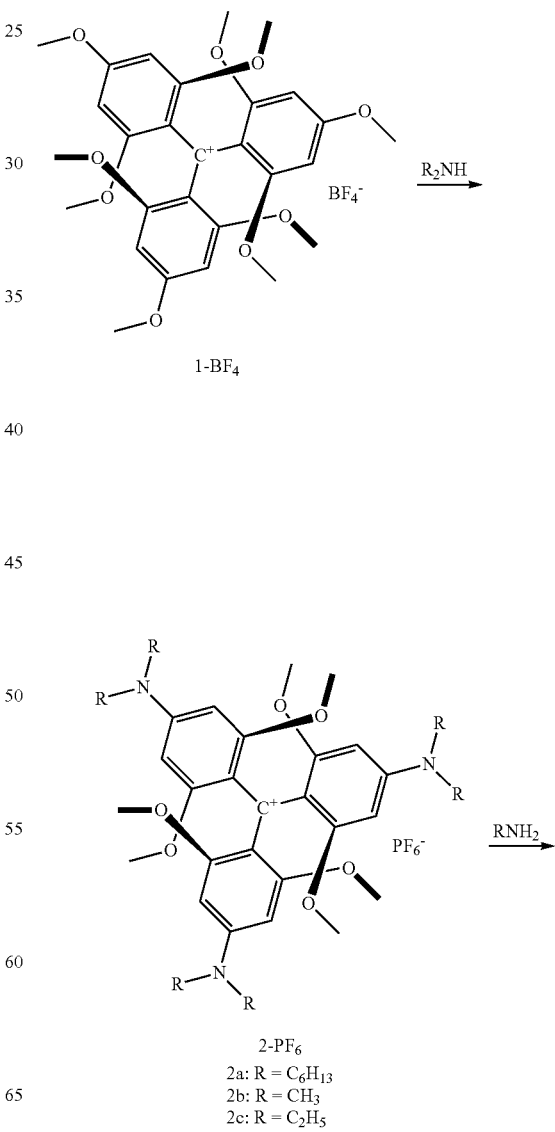

Scheme 2. Molecular structure of the pH responsive and the reference dyes.

2-PF$_6$
2a: R = C$_6$H$_{13}$
2b: R = CH$_3$
2c: R = C$_2$H$_5$

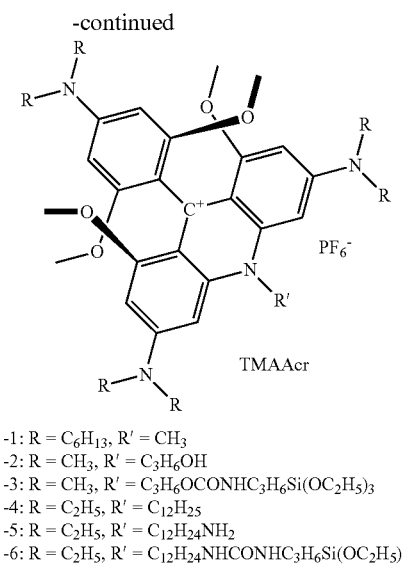

TMAAcr
-1: R = C$_6$H$_{13}$, R' = CH$_3$
-2: R = CH$_3$, R' = C$_3$H$_6$OH
-3: R = CH$_3$, R' = C$_3$H$_6$OCONHC$_3$H$_6$Si(OC$_2$H$_5$)$_3$
-4: R = C$_2$H$_5$, R' = C$_{12}$H$_{25}$
-5: R = C$_2$H$_5$, R' = C$_{12}$H$_{24}$NH$_2$
-6: R = C$_2$H$_5$, R' = C$_{12}$H$_{24}$NHCONHC$_3$H$_6$Si(OC$_2$H$_5$)$_3$

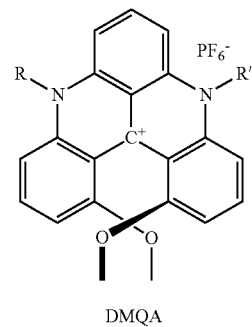

DMQA
-1: R = R' = C$_8$H$_{17}$
-2: R = CH$_3$, R' = C$_3$H$_6$OCONHC$_3$H$_6$Si(OC$_2$H$_5$)$_3$

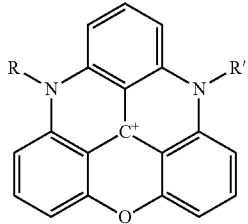

DAOTA
-1: R = C$_7$F$_3$O, R' = C$_3$H$_6$OCONHC$_3$H$_6$Si(OC$_2$H$_5$)$_3$
-2: R = C$_7$F$_3$O, R' = C$_{12}$H$_{25}$

Stability

Table 2. Leaking of 5(6)-carboxyfluorescein (CF), DMQA-2, DAOTA-1, and 6-stearamido-fluorescein (AF18) from the ETEOS-GPTMS matrix given as fluorescence intensity measured from a PBS solution at pH 7 surrounding a glass slide coated with ETEOS-GPTMS-dye matrix using maximum sized slit widths at the emission and excitation sites of the spectrometer.

| Dye | Intensity (a.u.) | Leaking Period | pH | pK$_a$ |
|---|---|---|---|---|
| CF | >>800 | 2 h | 7.0 | 6.5 |
| DMQA-2 | 0 | 15 h | 7.0 | — |
| DAOTA-1 | 80 | 15 h | 7.0 | 6.5 |
| AFC18 | 100 | 4 d | 7.0 | 6.5 |

Figure 2:
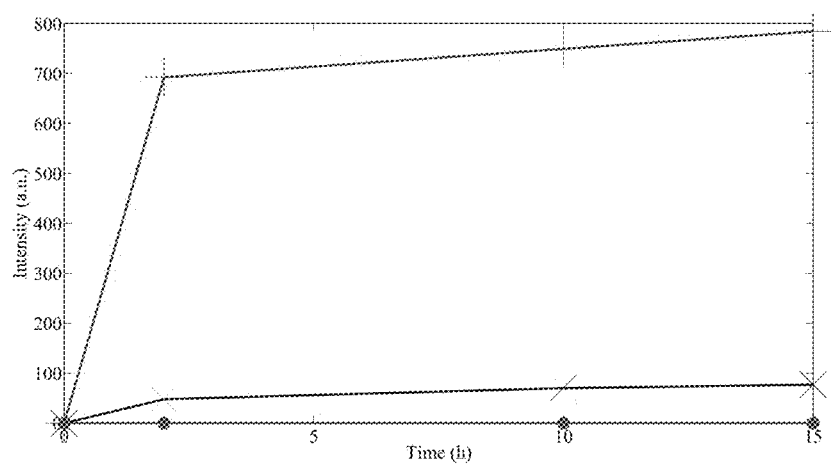
FIG. 2 shows the leakage over time of sensor spots.

FIG. 2 shows leakage over time of sensor spots: non-bound 5(6)-carboxyfluorescein (plus-signs), covalently bound DAOTA-1 (crosses), and covalently bound DMQA-2 (dots).

FIG. 2 shows the performance in leakage studies, against the performance of molecules without anchoring groups, and the data are collected in table 2. Leaking of the dyes entrapped or bound to the matrix was investigated by measuring the emission intensity from a PBS solution at pH 7.0 surrounding a non-bound dye (5(6)-carboxy fluorescein, CF), covalently bound (DMQA-2 and DAOTA-1) using the largest possible slit widths on the excitation and emission sites of the spectrometer and an excitation wavelength of 450 nm, these data are shown in FIG. 2. While the physically bound dye and 6-stearamido-fluorescein (AF18) was also tested, we did not record the transient curve. All the leakage data is compiled in table 2. The results reveal that DAOTA-1 leaked to a small extend, which we, based on NMR data, can assign to a fraction of un-linked dye in the ETEOS-GPTMS matrix, this issue has previously been reported for fluorescein, which was only partially activated. The compound DMQA-2 could based on NMR data be shown to be 100% activated and did as a consequence not show any leakage. This shows that effective binding can indeed be obtained in the ETEOS-GPTMS matrix and leakage can be avoided completely by fully activating the dye for polymerization. The unbound CF showed extensive leakage and the data in table 2 is obtained using half the sizes of the slit widths as those used for DMQA-2 and DAOTA-1.

Figure 3:
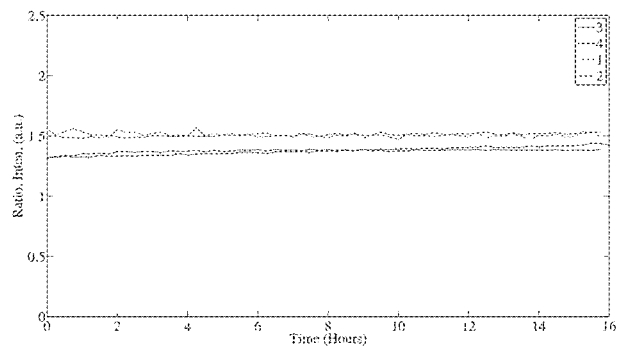
FIG. 3 shows the development over time for the ratiometric signal in four different buffer solutions.

To evaluate the photostability of the sensor we performed a 16-hour scan, see FIG. 3. No perceivable slope of the curves could be seen in this time interval, which proves that this system has a very high long-term stability under constant irradiation.

FIG. 3 shows the development in the ratiometric signal in four different buffer solutions at pH 3 during 16 h of irradiation at 525 nm of a DAOTA/DMQA based sensor.

Sensor Action

The performance of the sensors is shown as titration curves in FIG. 4. The spectra behind the titration curves are shown in FIG. 5. It is clear that a pH-dependent sensor action is achieved for these two sensor systems. For the examples given in FIGS. 4 and 5 the pKa values are ~5, the data for all prepared sensors are compiled in table 1, sensors with a pK$_a$ from 1.1 to 6.7 was made.

Figure 4A:
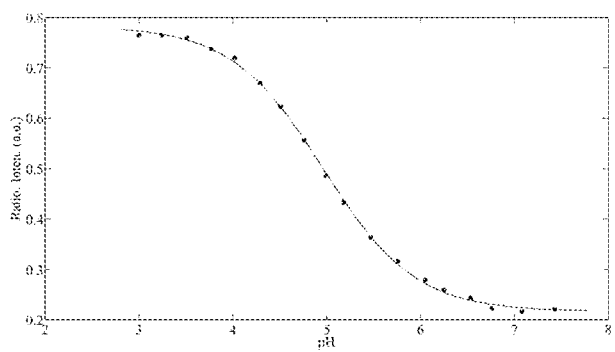
FIG. 4a shows TMAAcr-4 immobilised in the GPTMS-ETEOS matrix via lipophilic entrapment.
Figure 4B:
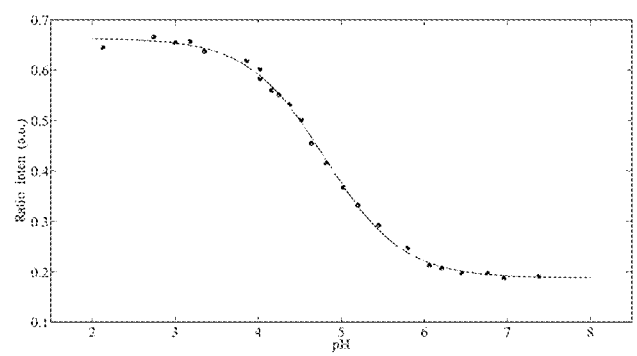
FIG. 4b shows TMAAcr-6 immobilised in the GPTMS-ETEOS matrix via covalent entrapment.

FIG. 4a shows the ratiometric pH response of TMAAcr-4 immobilized in GPTMS-ETEOS matrix via lipophilic entrapment. FIG. 4b shows the pH response of TMAAcr-6 immobilized in the GPTMS-ETEOS matrix via covalent entrapment. The pK$_a$ values of TMAAcr-4 and TMAAcr-6 are determined to 4.9 (lipophilic entrapment) and 4.8 (covalent entrapment).

Figure 5A:
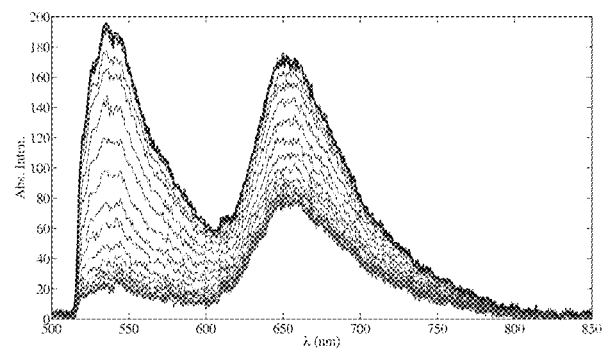
FIG. 5a shows the emission spectra of a GPTMS-ETEOS matrix with TMAAcr-4 and DMQA-1 lipophilic entrapped in the matrix.
Figure 5B:
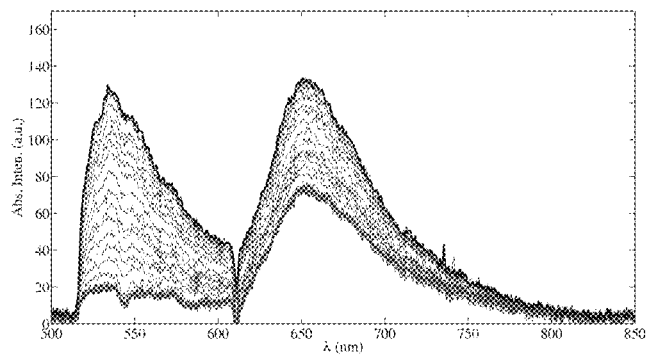
FIG. 5b shows the emission spectra of the GPTMS-ETEOS matrix with TMAAcr-6 covalently and DMQA-1 lipophilic entrapped in the GPTMS-ETEOS matrix.

FIG. 5 shows spectra of the sensors in action. FIG. 5a shows the emission spectra of a GPTMS-ETEOS matrix with TMAAcr-4 and DMQA-1 lipophilic entrapped in the GPTMS-ETEOS matrix at different pH values between 3 (black) and 7.5 (red). FIG. 5b shows emission spectra of a GPTMS-ETEOS matrix with TMAAcr-6 covalently and DMQA-1 lipophilic entrapped in the GPTMS-ETEOS matrix at different pH values between 2 (black) and 7.5 (red). Excitation at 475 nm±25 nm.

In order to evaluate the response time the temporal evolution of the detected signal (intensity ratio) was monitored, when the sensor was monitoring a solution where the pH was changed drastically as well as moderately. FIG. 6 shows the result, each panel shows the response of different matrices. It is clear that the response of the Lewis acid catalyzed sol-gel is much faster than the others tested. To highlight the differences an overlay is shown in FIG. 7. All the data are compiled in table 3. The alkyltrialkoxy-GPTMS matrixes have by far the fastest response times, showing some hysteresis, with a response going from high pH to low pH of ~10 s and going from low pH to high pH of ~20 s. Propyltrialkoxy silane derived matrices are faster responding than the ethyltrialkoxy silane derived matrices when the signal level of 90% is considered, while the full response occur on a similar timescale for both matrices.

Figure 6A:
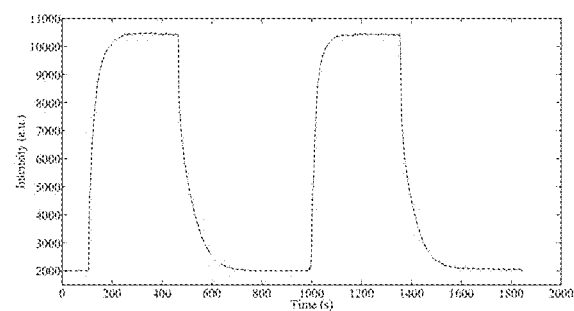
FIG. 6a shows the response time in PhTEOS-GPTMS matrix.
Figure 6B:
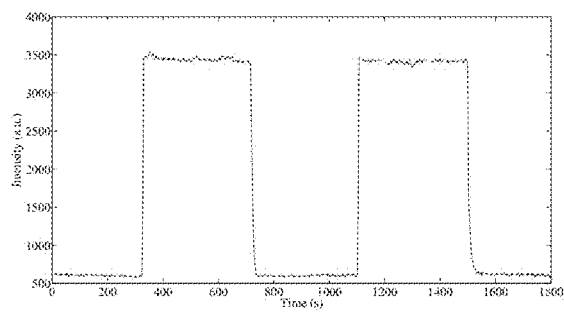
FIG. 6b shows the response time for ETEOS-GPTMS matrix.
Figure 6C:
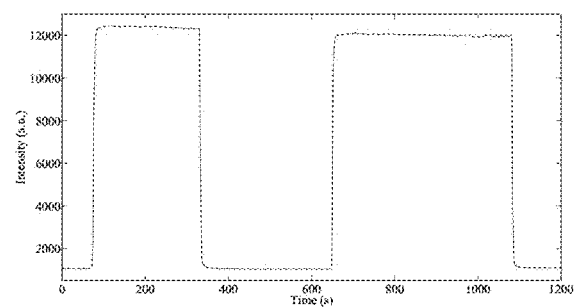
FIG. 6c shows the response time for the PrTEOS-GPTMS matrix.
Figure 7:
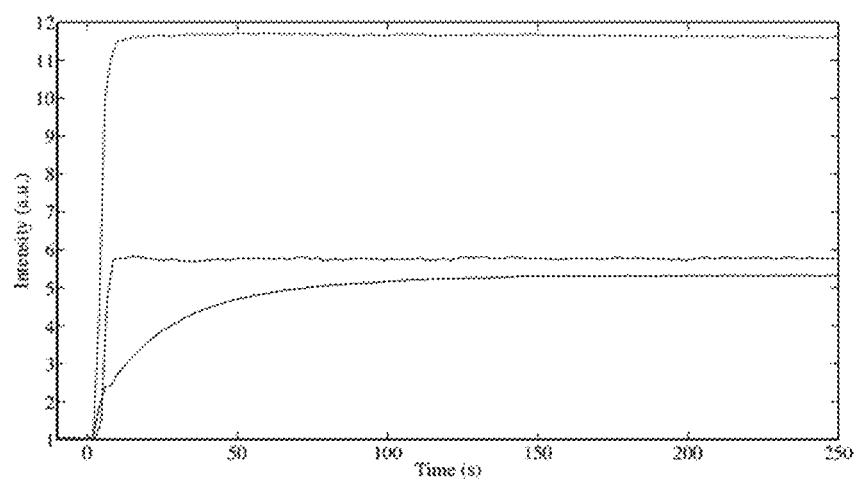
FIG. 7 discloses the response time of the pH active dye DAOTA-2 in an ETEOS-GPTMS matrix, compared to a matrix PVA and PEG-DA.
Figure 8:
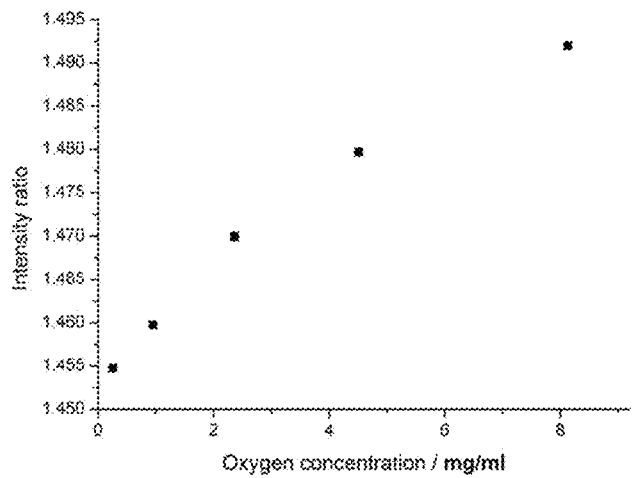
FIG. 8 discloses the intensity ratio of lipophil bounded DQMA and a ruthenium kompleks (Tris(4,7-diphenyl-1,10-phenanthroline)ruthenium(II) bis(hexafluorophosphate) kompleks CAS Nummer 123148-15-2) measured by ratiometic titration (I(Ru)/I(DMQA)) in aqueous solutions having different oxygen concentrations. The measurements are determined with an optical DO electrode from Mettler-Toledo.

FIG. 6 shows the response time of pH-active dye DAOTA-2 in a PhTEOS-GPTMS (FIG. 6a), an ETEOS-GPTMS (FIG. 6b) and PrTEOS-GPTMS (FIG. 6c) matrices. High intensity: Low pH (<2). Low intensity: High pH (>10).

FIG. 7 shows the response time of pH active dye DAOTA-2 in an ETEOS-GPTMS (red), PVA (blue) and PEG-DA (green) matrix. High intensity: Low pH (<2). Low intensity: High pH (>10).

Table 3. The response times ($t_{90}$ and $t_{100}$) given in seconds (s) of the ETEOS-GPTMS, PrTEOS-GPTMS, and PhTEOS-GPTMS matrices with of the pH-active dye DAOTA-2 incorporated, and the response times of PVA film and PEG-DA hydrogel with the pH-active dye TMAAcr-4 incorporated. H-L refers to the response time going from high (H) pH (>10) to a low (L) pH (<2) value, L-H has the opposite meaning. Numbers in parentheses refer to response times measured in the ETEOS-GPTMS matrix with the dyes DAOTA-1 and DMQA-2 covalently bound.

| Matrix | Dye | $t_{90}$ (H-L)/s | $t_{100}$ (H-L)/s | $t_{90}$ (L-H)/s | $t_{100}$ (L-H)/s |
|---|---|---|---|---|---|
| PhTEOS-GPTMS | DAOTA-2 | 59 | 171 | 108 | 271 |
| ETEOS-GPTMS | DAOTA-2 | 9 | 24 | 19 | 40 |
|  | (DAOTA-1 DMQA-2) | (10) | (30) | (23) | (47) |
| PrTEOS-GPTMS | DAOTA-2 | 6 | 34 | 7 | 31 |
| PVA | TMAAcr-4 | 6 | 50 | 25 | 55 |
| PEG-DA | TMAAcr-4 | 40 | 98 | 192 | 262 |

CONCLUSION

We have shown that our system has a shorter or comparable response time than what was previously reported and a high degree of photostability. Furthermore, with this sensor we have solved the leaking issue, using either covalent attachment or lipophilic entrapment of the active components. We have also shown that the activation of the active component is important in making leakage free film.

REFERENCES AND FOOTNOTES

1. P. C. Jeronimo, A. N. Araujo and B. S. M. M. M. Conceicao, *Talanta*, 2007, 72, 13-27.
2. S. M. Borisov and O. S. Wolfbeis, *Chemical Review*, 2008, 108, 423-461.
3. C. McDonagh, C. S. Burke and B. D. MacCraith, *Chemical Review*, 2008, 108, 400-422.
4. O. S. Wolfbeis, *Anal. Chem.*, 2008, 80, 4269-4283.
5. X. D. Wang and O. S. Wolfbeis, *Anal Chem*, 2013, 85, 487-508.
6. A. Lobnik, I. Oehme, I. Murkovic and O. S. Wolfbeis, *analytica Chemica Acta*, 1998, 367, 159-165.
7. M. D. Senarath-Yapa and S. S. Saavedra, *Analytica chimica acta*, 2001, 432, 89-94.
8. M. Cajlakovic, A. Lobnikb and T. Werner, *Analytica chimica acta*, 2002, 455, 207-213.
9. S. R. Adams, A. T. Harootunian, Y. J. Buechler, S. S. Taylor and R. Y. Tsien, *Nature*, 1991, 349, 694-697.
10. D. Wencel, B. D. MacCraith and C. McDonagh, *Sensors and Actuators B: Chemical*, 2009, 139, 208-213.
11. D. Wencel, M. Barczak, P. Borowski and C. McDonagh, *J. Mater. Chem.*, 2012, 22, 11720.
12. P. Innocenzi, G. Brusatin, M. Guglielmi and R. Bertani, *Chem. Mater.*, 1999, 11, 1672-1679.
13. P. Innocenzi, G. Brusatin and F. Babonneau, *Chem. Mater.*, 2000, 12, 3726-3732.
14. D. Wencel, J. P. Moore, N. Stevenson and C. McDonagh, *Anal Bioanal Chem*, 2010, 398, 1899-1907.
15. T. M. Butler, B. D. MacCraith and C. McDonagh, *Journal of Non-Crystalline Solids* 1998 224 249-258.
16. P. J. SKRDLA, S. S. SAAVEDRA and N. R. ARMSTRONG, *applied spectroscopy*, 1999, 53, 785-791.
17. G. BRUSATIN, P. INNOCENZI and M. GUGLIELMI, *Journal of Sol-Gel Science and Technology*, 2003, 26, 303-306.
18. B. W. Laursen, F. C. Krebs, M. F. Nielsen, K. Bechgaard, J. B. Christensen and N. Harrit, *J. Am. Chem. Soc.*, 1998, 120, 12255-12263.
19. J. C. Martin and R. G. Smith, *J. Am. Chem. Soc.*, 1964, 86, 2252-2256.

The invention claimed is:

1. A method for the production of a sol-gel based matrix comprising the steps of:
   a) providing a first alkoxysilane of the general formula:

$R^1-Si(OR^2)_3$ and a second alkoxysilane of the general formula:

$$\underset{O}{\triangle}-R^3-Si(OR^2)_3$$

wherein
   $R^1$ represents a straight or branched $C_1$-$C_6$ alkyl or $C_2$-$C_6$ alkenyl, a $C_3$-$C_6$ cycloalkyl, a $C_1$-$C_6$ aminoalkyl, a $C_1$-$C_6$ hydroxyalkyl, a $C_1$-$C_6$ cyanoalkyl, a phenyl, a group of the formula —Y—(X—Y)$_n$H, wherein Y independently is selected from straight or branched $C_1$-$C_6$ alkylene, X is a hetero atom or group selected among O, S, NH, and n is an integer of 1-5,
   or $R^1$ represents a $C_1$-$C_6$ alkyl substituted with a group Z, wherein Z independently is selected form the group comprising hydrogen, cyano, halogen, hydroxy, nitro, amide $C_1$-$C_{24}$-alkyl, $C_1$-$C_{24}$-haloalkyl, $C_2$-$C_{24}$-alkenyl, $C_2$-$C_{24}$-alkynyl, aryl, $C_1$-$C_{24}$-alkoxy, $C_1$-$C_{24}$-alkylsulfonyl, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester comprising a $C_1$-$C_6$ alkyl alcohol moiety, (carboxyl ester)amino comprising a $C_1$-$C_6$ alkyl alcohol moiety, (carboxyl ester)oxy comprising a $C_1$-$C_6$ alkyl alcohol moiety, sulfonyl, sulfonyloxy, thiol, thiocarbonyl, $C_1$-$C_{24}$-alkylthio, 5 or 6 membered heteroaryl, or a $C_3$-$C_7$ cycloalkyl;
   $R^2$ independently represents a straight or branched $C_1$-$C_6$ alkyl; and
   $R^3$ represents a linker chosen from a group of the formula —$R^4$—(X—$R^4$)$_n$— wherein R⁴ independently is selected from straight or branched $C_2$-$C_6$ alkylene, $C_2$-$C_{24}$-haloalkylene, X is a hetero atom or group selected among O, S, NH, and n is an integer of 0-12, b) preparing a first sol-gel component by polymerisation of the first alkoxysilane in the presence of an acid catalyst, c) preparing a second sol-gel component by polymerisation of the second alkoxysilane in the presence of Lewis acid catalyst, wherein an additional alkoxysilane is added in at least one of steps b) or c), said additional alkoxysilane being of the formula:

$$R^5\text{—}Si(OR^2)_3$$

wherein $R^2$ is as defined above and $R^5$ represents a group having covalently attached an indicator or reference dye, d) Mixing the first sol-gel component and the second sol-gel component for the preparation of a sol-gel based matrix.

2. The method according to claim 1, wherein $R^5$ is of the general formula $$\text{—}R^3\text{—}NH\text{—}C(\!=\!O)\text{—}X\text{—}R^3\text{-}Q$$

wherein $R^3$ is as defined above and independently selected, and Q represents an indicator and/or a reference dye.

3. The method according to claim 2, wherein Q is an indicator dye derived from 8-hydroxypyrene-1,3,6-trisulfonic acid (HPTS), fluorescein, or rhodamine B.

4. The method according to claim 2, wherein Q is a reference dye derived from triangulenium compounds, acridinium compounds, ruthenium doped sol-gel particles, ruthenium-based compounds with α-diimine ligands, porphorin with Pt or Pd as the central metal atom, $Ru(bpy)_2(dpp)Cl_2$, $Ru(bpy)_3Cl_2$, a lanthanide containing complex, or polymeric metal containing structure.

5. The method according to claim 1, wherein the Lewis acid catalyst is selected from the group consisting of $TiCl_3$, $AlCl_3$, and $BF_3$, or solvates or etherates thereof.

6. The method according to claim 1,
wherein one of a reference dye or an indicator dye is added to the first sol-gel component of step b) and the other one of a reference dye or indicator dye is added to the second sol-gel component of step c).

7. The method according to claim 1, wherein the first alkoxysilane is selected from the group consisting of ethyltriethoxysilane (ETEOS), methyltriethoxysilane (MTEOS), propyltriethoxysilane (PrTEOS), n-octyltriethoxysilane (n-octyl TEOS), methyltrimethoxysilane (MTMOS), aminopropyltrimethoxysilane (APTMOS), phenyltriethoxysilane (PhTEOS), and phenyl trimethoxysilane (PhTMOS).

8. The method according to claim 1, wherein the second alkoxysilane is selected from the group consisting of 3-glycidoxypropyltrimethoxysilane (GPTMS).

9. The method according to claim 1, wherein the additional alkoxysilane is added to the first sol-gel component in step b).

10. The method according to claim 1, wherein the additional alkoxysilane is added to the second sol-gel component in step c).

11. The method according to claim 9, wherein the first sol-gel component is allowed to polymerize for at least 15 minutes before the additional alkoxysilane is added.

12. The method according to claim 10, wherein the second sol-gel component is allowed to polymerize for at least 15 minutes before the additional alkoxysilane is added.

* * * * *